United States Patent [19]

Christman et al.

[11] Patent Number: 5,670,314
[45] Date of Patent: Sep. 23, 1997

[54] GENETIC ALTERATIONS THAT CORRELATE WITH LUNG CARCINOMAS

[75] Inventors: Michael F. Christman; Joe W. Gray; Nikki A. Levin; Pius Brzoska, all of San Francisco, Calif.; Haruhiko Nakamura, Yokohama, Japan

[73] Assignee: Regents of the University of California, Oakland, Calif.

[21] Appl. No.: 199,772

[22] Filed: Feb. 22, 1994

[51] Int. Cl.$^6$ ..................................................... C12Q 1/68
[52] U.S. Cl. ................................................ 435/6; 436/811
[58] Field of Search ............................... 435/6; 935/77, 935/78; 436/811, 813

[56] References Cited

PUBLICATIONS

Wurster–Hill, et al. (1984) "Cytogenetics of Small Cell Carcinoma of the Lung", *Cancer Genetics and Cytogenetics,* 13:303–330.
Zech, Lore, et al. (1985) "Karyotypic Characterization of Established Cell Lines and Short–Term Cultures of Human Lung Cancers", *Cancer Genetics and Cytogenetics,* 15:335–347.
Birrer, Michael J., et al. (1992) "Application of Molecular Genetics to the Early Diagnosis and Screening of Lung Cancer", *Cancer Research (Suppl.,),* 52:2658s–2664s.
Brooks, Burke J., et al. (1987) "Amplification and Expression of the myc Gene in Small–Cell Lung Cancer", *Advances in Viral Oncology,* 7:155–172.
Carbone, David P., et al. (1992) "The Molecular Genetics of Lung Cancer", *Advances in Internal Medicine,* 37:153–171.
Griffin, Constance A., et al. (1985) "Expression of the c–myb Oncogene in Human Small Cell Lung Carcinoma", *Cancer Research,* 45:272–275.
Ibson, J.M., et al. (1987) "Oncongene Amplification and Chromosomal Abnormalities in Small Cell Lung Cancer", *Journal of Cellular Biochemistry,* 33:267–288.
Morstyn, George, et al. (1987) "Heterogeneous Cytogenetic Abnormalities in Small Cell Lung Cancer Lung Lines", *Cancer Research,* 47:3322–3327.
Whang–Peng, Jacqueline (1989) 3p Deletion and Small Cell Lung Carcinoma (editorial), *Mayo Clinic Proc,* 64:256–260.
Takeda et al, Human Mutation 2(2):112–117 (1993) (Biosis Abstract).
Cline et al, Cancer 60(11):2669–74 (1987) (Biosis Abstract).
Little et al, Nature 306:194–196 (1983).
Miura et al, Cancer Res 52:1322–1328 (1992).
Brauch et al, N.Engl.J.Med 317:1109–13 (1987).
Takahashi et al, Science 246:491–494 (1989).
Pollard–Knight, J.Meth.Cell.Mol.Biol 2:(3): 113–132 (1990).

*Primary Examiner*—Eggerton A. Campbell
*Attorney, Agent, or Firm*—Townsend and Townsend and Crew LLP

[57] ABSTRACT

The present invention relates to compositions and methods for detecting chromosome abnormalities correlated with lung cancer. The method contacting a nucleic acid sample from a patient with a probe which binds selectively to a target polynucleotide sequence correlated with lung cancer.

14 Claims, 5 Drawing Sheets

| GREEN TO RED FLUORESCENCE RATIO | COPY NUMBER CHANGE |

INCREASES: 8q21-22, 8q24.2-24.3
DECREASE: 8p

INCREASE: 5p

DECREASE: 3p11-24

DECREASE: 4q22-35

NONE

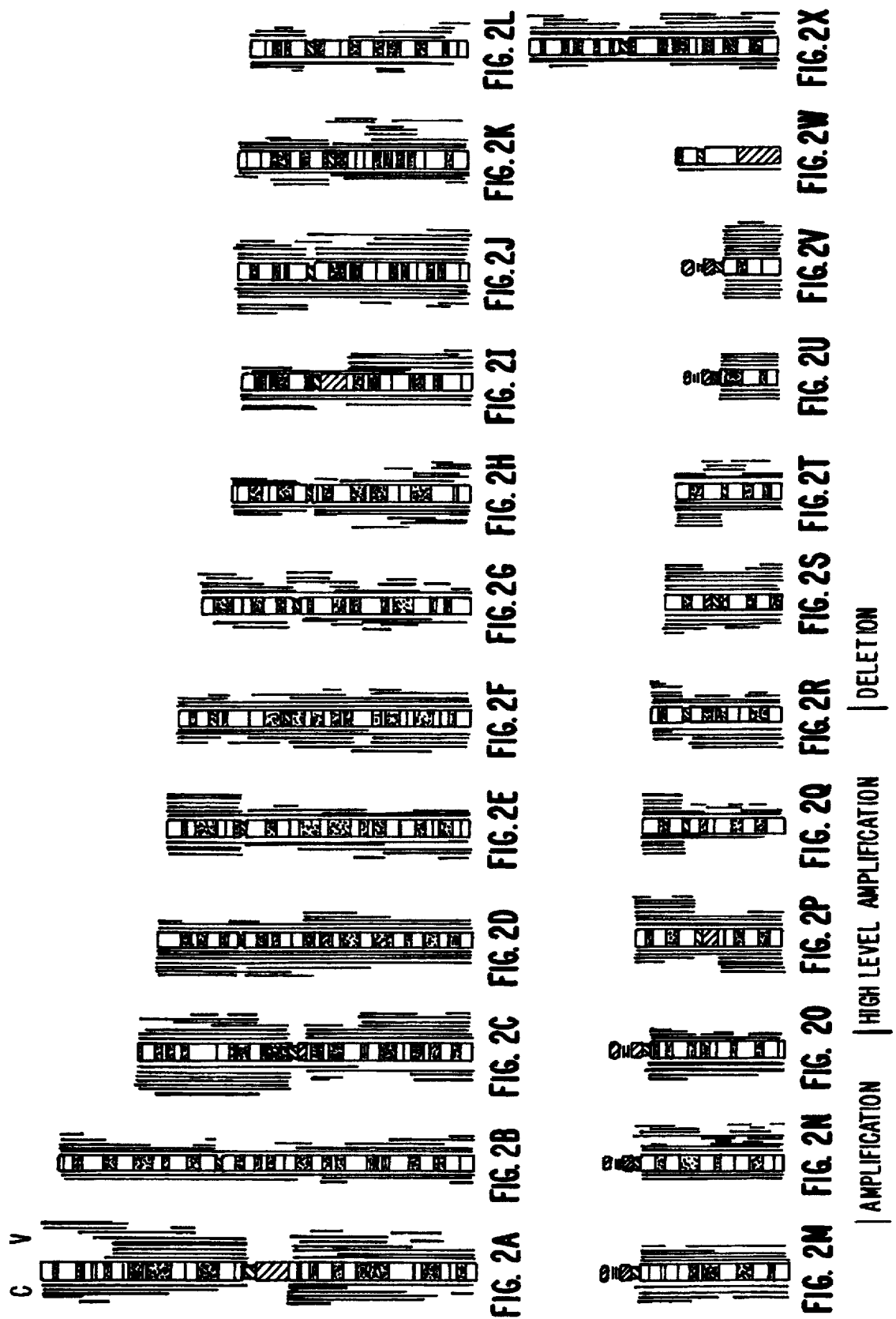

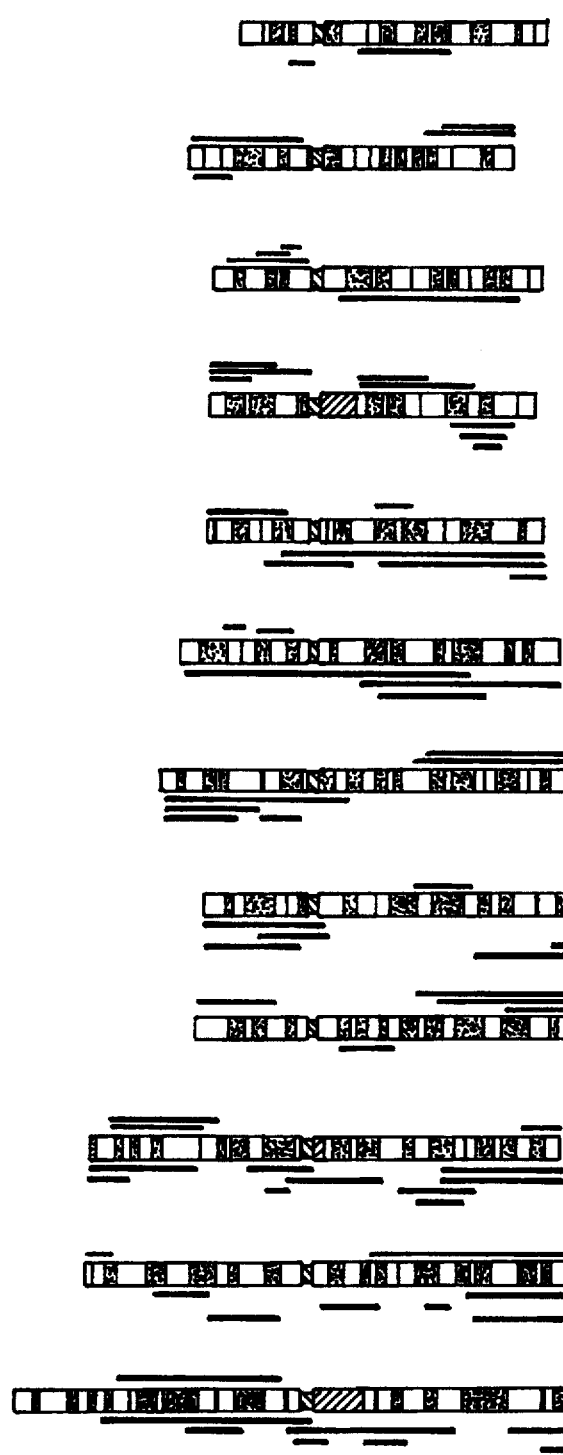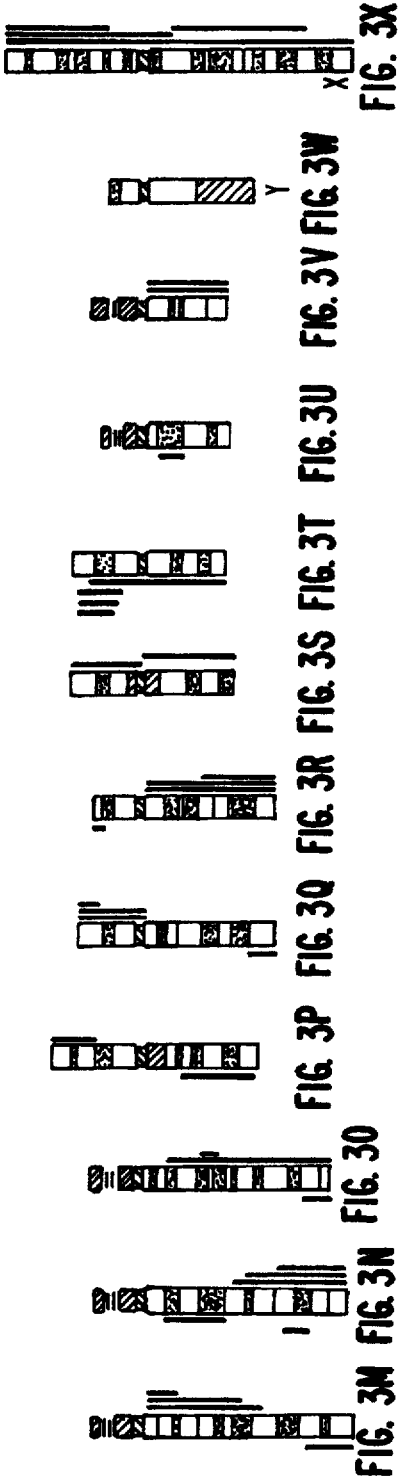

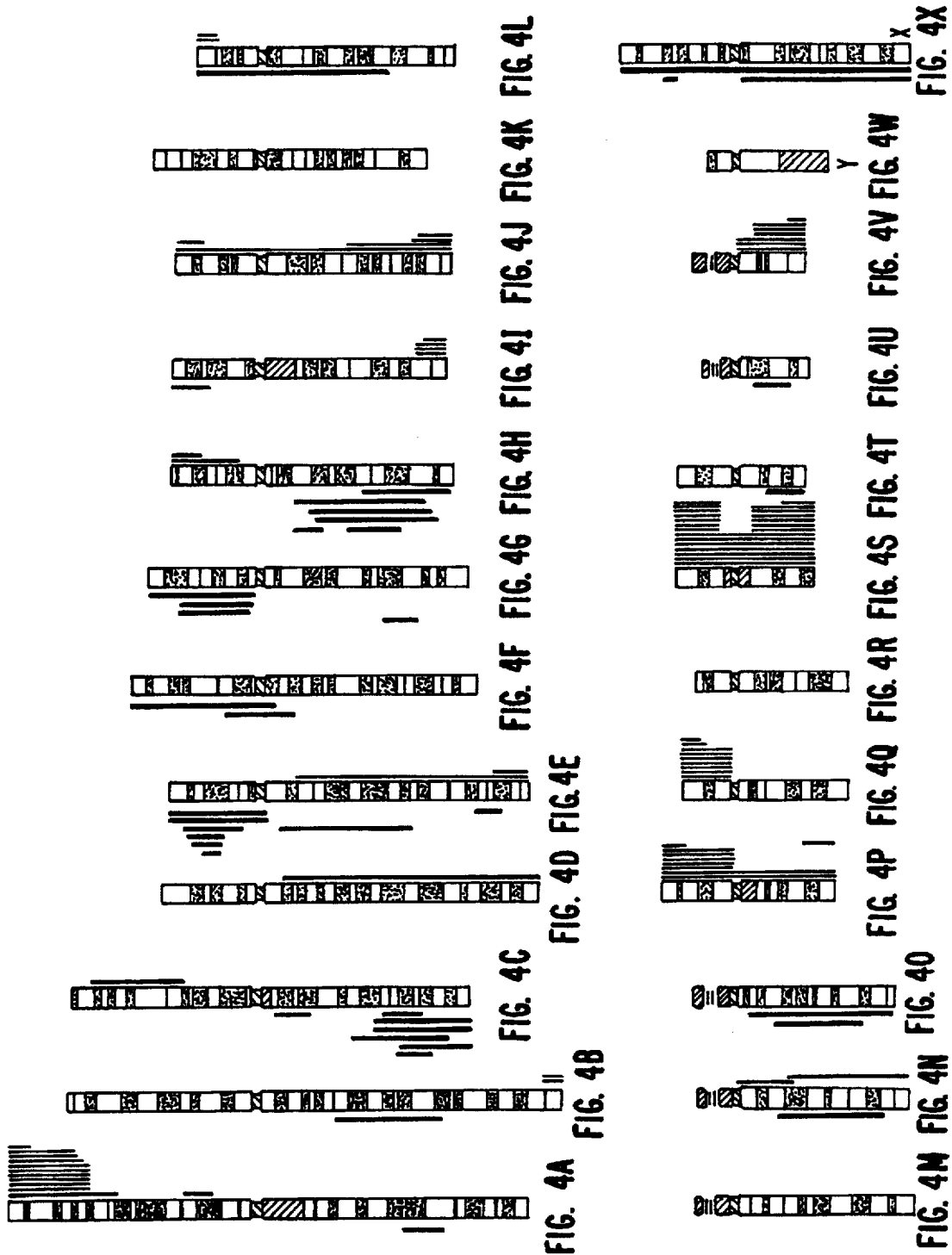

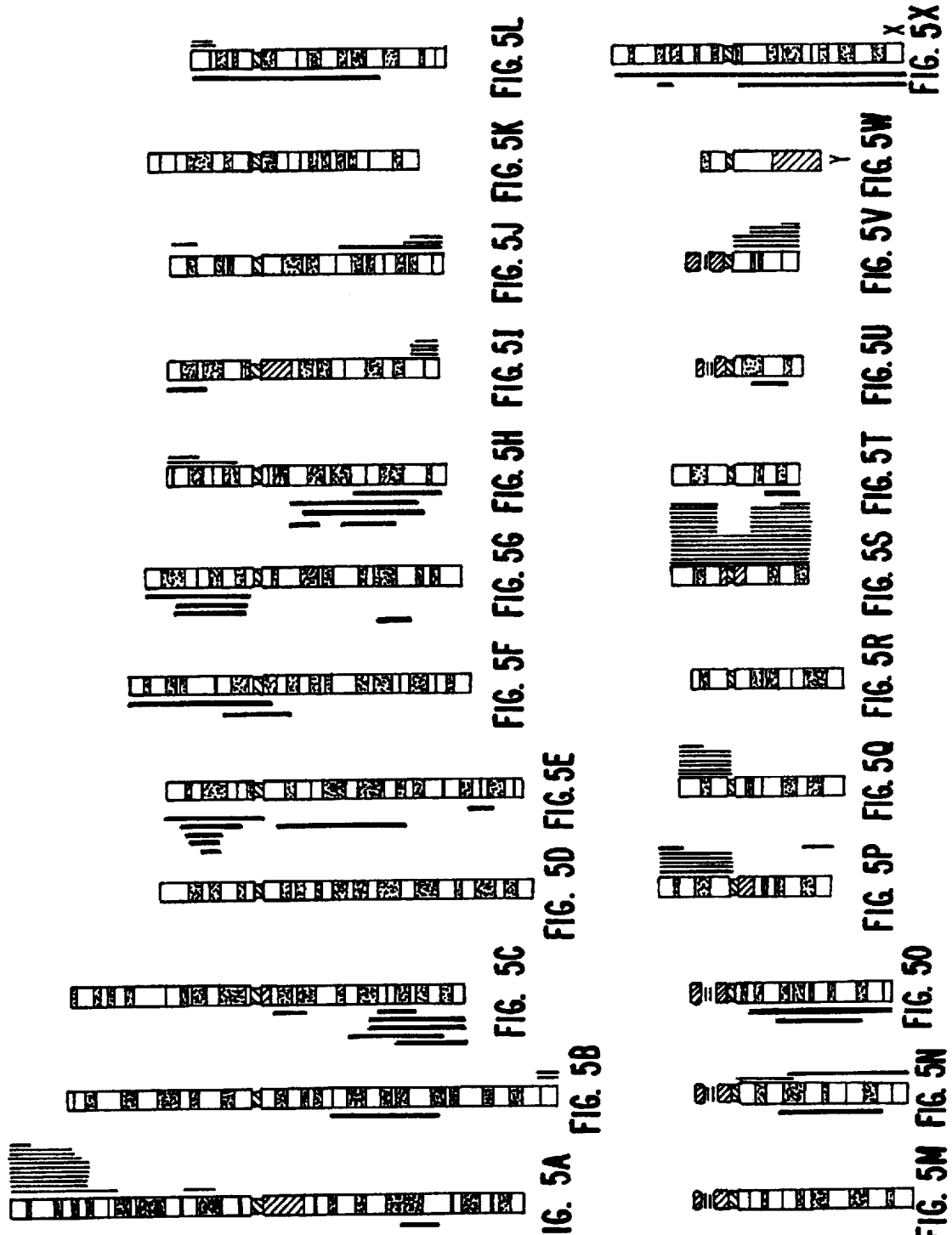

GENETIC ALTERATIONS THAT CORRELATE WITH LUNG CARCINOMAS

BACKGROUND OF THE INVENTION

The present invention provides methods for detecting DNA copy number changes associated with neoplastic growth. In particular, it provides methods and compositions for the localization of chromosomal regions of amplification or deletion associated with lung cancers.

Over 140,000 new cases of lung cancer are diagnosed each year, making lung cancer the most common cause of cancer-related death in the United States (Johnson and Greco, *Crit. Rev. Onc. Hemat.* 4:303–336 (1986)). One fourth of lung cancer cases are classified as "small cell lung carcinoma" (SCLC), which is distinguished from a variety of cancers referred to as "non-small cell lung cancer" (N-SCLC) based on histology, biochemical markers and clinical behavior. Major treatment decisions are made on the basis of the histological classification of a tumor as SCLC or N-SCLC.

The majority of patients with SCLC have metastases at the time their cancer is diagnosed. Despite the fact that SCLC initially shows great sensitivity to radiation therapy and chemotherapy, most patients relapse and die from their tumors within two years of diagnosis (Sieffer and Ihde, *Seminars in Oncology* 15:278–299 (1988)). Although the introduction of combination chemotherapy and radiotherapy to the treatment of SCLC has greatly improved the average survival time of patients with this disease, the prognosis is still very poor (Viallet and Ihde, *Crit. Rev. Onc. Hemat.* 11:109–135 (1991)).

In contrast, N-SCLC are typically found to be localized at the time of presentation and are generally considered for either surgery or radiotherapy. The response of N-SCLC to chemotherapy usually is not dramatic. This therapy is less important in metastatic disease than it is in SCLC.

Increased understanding of the genetics of tumorigenesis and response to radiation of lung cancers will lead to better techniques of early diagnosis and for the prediction of response to radiotherapy. For example, improved techniques for the early diagnosis of SCLC based on detection of early genetic aberrations may allow earlier treatment (Birrer and Brown *Cancer Res.* (Suppl.) 52:2658s–2664s (1992)) before metastasis has occurred. Identification of genetic aberrations that correlate with radioresponse may lead to an assay that will allow stratification of patients into groups that will benefit from more (or less) aggressive radiotherapy or that will be candidates for other therapeutic modalities.

Several genetic alterations have been identified in both SCLC and N-SCLC tumors, including changes in known oncogenes and tumor suppressor genes (see, e.g., Birrer and Brown, supra) aneusomies, translocations, regional chromosomal deletions, heterogeneously staining regions and double minute (DM) chromosomes (Wurster-Hill et al., *Cancer Gen. Cytogen* 13:303–330 (1984); Ibson et al., *J. Cell. Biochem* 33:267–288 (1987)); Morstyn et al., *Cancer Res.* 47:3322–3327 (1987)). With the exception of RB, a putative tumor suppressor on 3p, and possibly p53, none of the alterations identified so far are good candidates for the earliest events in the progression of SCLC and none correlate well with tumor response to radiotherapy.

The detection of amplified or deleted chromosomal regions has traditionally been done by cytogenetics. In complex karyotypes with multiple translocations and other genetic changes, traditional cytogenetic analysis is of little utility because karyotype information is lacking, or cannot be interpreted. Teyssier, J. R., *Cancer Genet. Cytogenet.* 37:103 (1989). Furthermore, conventional cytogenetic banding analysis is time consuming, labor intensive, and frequently difficult or impossible.

Comparative genomic hybridization (CGH) is a more recent approach to identify the presence and localization of amplified or deleted sequences. See, Kallioniemi, et al. *Science* 258:818 (1992) and WO 93/18186. CGH reveals amplifications and deletions irrespective of genome rearrangement. CGH can provide a quantitative estimate of DNA copy number and also provides information regarding the localization of amplified or deleted sequences in the normal chromosome.

The use of CGH and related techniques to identify the genetic events leading to neoplastic transformation involved in lung cancers can facilitate efforts to define the biological basis for disease, improve prognostication and prediction of therapeutic response, and permit earlier tumor detection. The present invention addresses these and other needs.

SUMMARY OF THE INVENTION

The present invention provides compositions and methods of detecting a chromosome abnormality correlated with lung cancer. The methods comprise contacting a nucleic acid sample from a patient with a probe which binds selectively to a target polynucleotide sequence correlated with lung cancer. The probe is contacted with the sample under conditions in which the probe binds selectively with the target polynucleotide sequence to form a hybridization complex. The formation of the hybridization complex is then detected.

Alternatively, sample DNA from the patient can be flourescently labeled and competitively hybridized against florescently labeled normal DNA to normal lymphocyte metaphases. Alterations in DNA copy number in the sample DNA are then detected as increases or decreases in sample DNA as compared to normal DNA.

The chromosome abnormality is typically a deletion or an amplification. The methods can be used to detect both small cell and non-small cell lung cancers.

Definitions

A "nucleic acid sample" as used herein refers to a sample comprising DNA in a form suitable for hybridization to a probes of the invention. For instance, the nucleic acid sample can be a tissue or cell sample prepared for standard in situ hybridization methods described below. The sample is prepared such that individual chromosomes remain substantially intact and typically comprises metaphase spreads or interphase nuclei prepared according to standard techniques.

The sample may also be isolated nucleic acids immobilized on a solid surface (e.g., nitrocellulose) for use in Southern or dot blot hybridizations and the like. In some cases, the nucleic acids may be amplified using standard techniques such as PCR, prior to the hybridization. The sample is typically taken from a patient suspected of having a lung cancer associated with the abnormality being detected.

As used herein a "probe" is defined as a polynucleotide (either RNA or DNA) capable of binding to a complementary target cellular genetic sequence through one or more types of chemical bonds, usually through hydrogen bond formation. It will be understood by one of skill in the art that probes will typically substantially bind target sequences lacking complete complementarity with the probe sequence depending upon the stringency of the hybridization conditions. The probes are preferably directly labelled as with isotopes or indirectly labelled such as with biotin to which a streptavidin complex or fluroescently labeled antibody may later bind. By assaying for the presence or absence of the probe, one can detect the presence or absence (or copy number) of the target. Nucleic acid probes can be prepared by a variety of methods known to those of skill in the art.

"Chromosome abnormalities" as used herein refers to any of several types well known to those of skill in the art, including, but not limited to, extra or missing individual chromosomes, extra or missing portions of a chromosome (segmental duplications or deletions), breaks, rings and chromosomal rearrangements. Chromosomal rearrangements include translocations, dicentrics, inversions, insertions, amplification and deletions.

A chromosome region or a target polynucleotide sequence is said to be correlated with lung cancer if deletion, amplification, or other rearrangement of the region is found in a significant proportion (typically greater than about 30%, usually greater than about 50%) of lung cancer cell lines or tumors.

"Bind(s) substantially" refers to complementary hybridization between an oligonucleotide and a target sequence and embraces minor mismatches that can be accommodated by reducing the stringency of the hybridization media to achieve the desired detection of the target polynucleotide sequence.

"Hybridizing" refers the binding of two single stranded nucleic acids via complementary base pairing.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

BRIEF DESCRIPTION OF THE DRAWINGS

FIG. 2 is a chromosome schematic depicting the regions of chromosomal amplification and deletion observed for classic and variant SCLC cell lines.

FIG. 3 is a chromosome schematic depicting the gains and losses/in non-small cell lung cancer cell lines.

FIG. 4 is a chromosome schematic depicting the gains and losses in primary small cell lung cancers.

FIG. 5 is a chromosome schematic depicting the gains and losses in primary N-SCLC.

DESCRIPTION OF THE PREFERRED EMBODIMENT

Figure 1A:
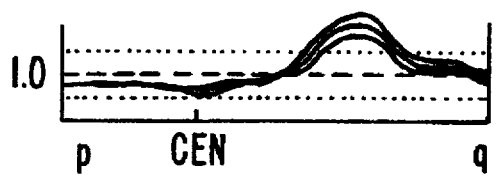
FIGS. 1A–E show sample green to red fluorescence ratio profiles generated by integration of the fluorescence intensity along the axis of FITC-avidin (a green fluorochrome) and anti-digoxigenin rhodamine (a red fluorochrome) visualized target chromosome.

The present invention is based on a comprehensive molecular cytogenetic analysis of the genomes of SCLC and N-SCLC cell lines and tumors using comparative genetic hybridization (CGH, Kallioniemi et al., supra). This technique is a variation of a fluorescence in situ hybridization (FISH) technique which allows the simultaneous examination of the entire genome of a given cell line or tumor for DNA copy number abnormalities in a single experiment.

The nucleotide sequences, typically DNA, used in the hybridization described below may be detectably labeled prior to the hybridization reaction. Alternatively, a detectable label may be selected which binds to the hybridization product. The nucleotide sequences may be labeled with any detectable group for use in practicing the invention. Such detectable group can be any material having a detectable physical or chemical property. Such detectable labels have been well-developed in the field of immunoassays and in general most any label useful in such methods can be applied to the present invention. Thus a label is any composition detectable by spectroscopic, photochemical, biochemical, immunochemical, or chemical means. Useful labels in the present invention include fluorescent dyes, electron-dense reagents, enzymes (as commonly used in an ELISA), biotin, dioxigenin, or haptens and proteins for which antisera or monoclonal antibodies are available. The particular label used is not critical to the present invention, so long as it does not interfere with the in situ hybridization of the sequence. In addition, the label must be detectable in as low a copy number as possible, thereby maximizing the sensitivity of the assay, and yet be detectable above any background signal. Finally, a label must be chosen that provides a highly localized signal thereby providing a high degree of spatial resolution. In a preferred embodiment, the label is digoxigenin-11-dUTP or biotin-14-dATP, which are then detected using fluorescence excitation.

The labels may be coupled to the DNA in a variety of means known to those of skill in the art. In a preferred embodiment the probe will be labeled using nick translation or random primer extension (Rigby, et al. *J. Mol. Biol.*, 113:237 (1977) or Sambrook, et al., *Molecular Cloning—A Laboratory Manual*, Cold Spring Harbor Laboratory, Cold Spring Harbor, N.Y. (1985)).

Standard in situ hybridization techniques are then used to probe a given sample (typically a metaphase spread). Hybridization protocols for the particular applications disclosed here are described in detail below. Several guides to the techniques are available, e.g., Gall et al. *Meth. Enzymol.*, 21:470–480 (1981) and Angerer et al. in *Genetic Engineering: Principles and Methods* Setlow and Hollaender, Eds. Vol 7, pgs 43–65 (plenum Press, New York 1985).

Briefly, a chromosomal sample is prepared by depositing cells, either as single cell suspensions or as tissue preparation, on solid supports such as glass slides and fixed by choosing a fixative which provides the best spatial resolution of the cells and the optimal hybridization efficiency.

Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application. Hybridization protocols for the particular applications disclosed here are described in detail below and in Pinkel et al. *Proc. Natl. Acad. Sci. USA*, 85:9138–9142 (1988), WO 93/18186 and EPO Pub. No. 430,402.

In some applications it is necessary to block the hybridization capacity of repetitive sequences. In this case, human genomic DNA is used as an agent to block such hybridization. The preferred size range is from about 200 bp to about 1000 bases, more preferably between about 400 to about 800 bp for double stranded, nick translated nucleic acids.

The FISH methods for detecting chromosomal abnormalities described herein can be performed on nanogram quantities of the subject nucleic acids. Paraffin embedded tumor sections can be used, as can fresh or frozen material. Because FISH and CGH can be applied to the limited material, touch preparations prepared from uncultured primary tumors can also be used (see, e.g., Kallioniemi, A. et al., *Cytogenet. Cell Genet.* 60:190–193 (1992)). For instance, small biopsy tissue samples from tumors can be used for touch preparations (see, e.g., Kallioniemi, A. et al., *Cytogenet. Cell Genet.* 60: 190–193 (1992)). Small numbers of cells obtained from aspiration biopsy or cells in bodily fluids (e.g., blood, urine, sputum and the like) can also be analyzed. For detection of lung cancers, sputum samples are particularly preferred.

In CGH, test (tumor) DNA uniformly labeled with a green fluorochrome and normal DNA uniformly labeled with a red fluorochrome are simultaneously hybridized to normal human metaphase chromosomes. Excess unlabeled repetitive DNA (e.g., Cot-1 DNA) included in the hybridization mixture inhibits hybridization of respective sequences that are interspersed throughout the genome or located at the chromosome centromeres. Increases and decreases in the green to red fluorescence ratio along each chromosome indicate regions of increased or decreased copy number in the tumor relative to normal DNA, respectively.

CGH was used to analyze 18 SCLC cell lines and 10 tumors and 5N-SCLC cell lines and 20 tumors to identify regions of the genome that contain previously unrecognized oncogenes and tumor suppressor genes, and other genes that play a role in tumorigenesis and/or radioresistance. The SCLC lines are categorized as "classic" or "variant" based on their cellular morphologies, growth phenotypes and enzymatic activities (Gazdar et al. *Cancer Research* 45:2924–2930 (1985)). Cell lines of the variant phenotype are also more resistant to killing by ionizing radiation than those of the classic phenotype (Carmichael, *Eur. J. Cancer Clin. Oncol.* 25:527–534 (1989)). These studies show several DNA copy number aberrations that have been identified previously and several that are novel. Importantly, 4 regions of common aberration correlate with response to radiation.

Genomic regions that are found to be sites of increased DNA copy number in a large fraction of the cell lines are likely to include oncogenes that are present at increased copy number and hence overexpressed. Overexpression of these genes may lead to uncontrolled growth. Regions that frequently show a decreased DNA copy number may contain tumor suppressor genes that through mutation of one allele and deletion on the other lead to loss of growth or organizational control (Weinberg, *Science* 254:1138–1146 (1992)). Of course, some of the DNA copy number abnormalities may arise as secondary consequences of general genomic instability resulting from the early stages of tumorigenesis. Such alterations are expected to occur randomly and, therefore, are not likely to be found in a high percentage of tumors and cell lines.

CGH generally detects unit changes in relative DNA content larger than about 10 Mb although smaller regions of increased copy can be detected if the level of increase is several-fold. In addition, CGH does not detect point mutations, small deletions or amplifications or genetic rearrangements, such as translocations. With these limitations in mind, changes identified here are referred to as DNA copy number increases and number decreases, rather than amplifications and deletions.

Copy number changes that affect whole chromosomes are most likely the result of aneuploidies. It is not surprising that many such changes were found as most of the cell lines used in this study are known to be near triploid or tetraploid with a wide range of chromosome numbers (Wurster-Hill et al. *Cancer Gen. Cytogen.* 13:303–330 (1984); Zech et al. *Cancer Gen. Cytogen.* 15:335–347 (1985)). However, cell lines with a perfect triploid or tetraploid genetic complement would appear normal by CGH as the relative numbers of each DNA sequence are the same as in a normal cell. A tetraploid cell line missing two copies of a given sequence would give the same CGH profile as a diploid cell line missing one copy. In these instance, the absolute level of a copy number change can be ascertained by using a single-copy probe for the affected region to perform FISH on the cell line in question, using the methods described below. However, in cases where a localized bright green band is observed on a chromosome arm and the fluorescence ratio profile shows a high-level peak, such alterations are considered to be amplifications.

The new regions of amplification or deletion described below can be studied in more detail using chromosome specific painting with a collection of probes that span the amplified or deleted region using the FISH techniques described above. For instance, a selected chromosome may be isolated by flow cytometry and then digested with restriction enzymes appropriate to give DNA sequences of at least about 20 kb and more preferably about 40 kb. Techniques of partial sequence digestion are well known in the art. See, for example Perbal, *A Practical Guide to Molecular Cloning* 2nd Ed., Wiley N. Y. (1988). The resulting sequences are ligated with vectors suitable for large DNA sequences such as cosmids, yeast artificial chromosomes (YACs), bacterial artificial chromosomes (BACs) and P1 phage. In addition, libraries spanning entire chromosomes are available commercially (Clonetech, South San Francisco, Calif.) or from the Los Alamos National Laboratory.

Once a probe library is constructed, a subset of the probes is physically mapped on the selected chromosome or chromosome region defined below. FISH and digital image analysis can be used to localize cosmids along the desired chromosome. This method is described in Lichter et al., *Science*, 247:64–69 (1990). Briefly, the clones are mapped by FISH to metaphase spreads from normal cells using e.g., FITC as the fluorophore. The chromosomes are counterstained by a stain which stains DNA irrespective of base composition (e.g., propidium iodide), to define the outlining of the chromosome. The stained metaphases are imaged in a fluorescence microscope with a polychromatic beam-splitter to avoid color-dependent image shifts. The different color images are acquired with a CCD camera and the digitized images are stored in a computer. A computer program is then used to calculate the chromosome axis, project the two (for single copy sequences) FITC signals perpendicularly onto this axis, and calculate the average fractional length from a defined position, typically the p-telomere.

Once a region of interest has been mapped using the probes, one of skill will recognize that there are numerous means of further defining and/or screening for this region. The region may be sequenced by digesting chromosomal DNA with restriction enzymes and identifying the specific duplication-bearing fragments using mapped cosmids as hybridization probes. The positive clones may then be subcloned into appropriate vectors and sequenced.

Sequence information permits the design of highly specific hybridization probes or amplification primers suitable for detection of the target sequences. This is useful for diagnostic screening systems as well as research purposes.

Means for detecting specific DNA sequences in a variety of diagnostic and other applications are well known to those of skill in the art. For instance, oligonucleotide probes chosen to be complementary to a select subsequence with the region can be used. Alternatively, sequences or subsequences may be amplified by a variety of DNA amplification techniques (for example via polymerase chain reaction, ligase chain reaction, transcription amplification, etc.) prior to detection using a probe. Amplification of DNA increases the sensitivity of the assay by providing more copies of possible target subsequences. In addition, by using labeled primers in the amplification process, the DNA sequences may be labeled as they are amplified.

The present invention further provides kits for the detection of the chromosomal abnormalities identified here. The kits comprise a compartment which contains a nucleic acid probe which binds selectively to a target polynucleotide sequence within these chromosomal aberrations. The probes may further comprise appropriate labels well known to those of skill in the art.

EXAMPLES

The following examples are provided by way of illustration only and not by way of limitation. Those of skill will readily recognize a variety of noncritical parameters which could be changed or modified to yield essentially similar results.

Example 1

Comparative Genomic Hybridization (CGH) Analysis of Small Cell Lung Carcinoma (SCLC) Cell Lines In order to detect genetic amplifications and deletions in SCLC cell lines, CGH was performed on SCLC cell lines using DNA from normal human male lymphocytes for comparison. Excess unlabeled blocking DNA was used to insure specificity.
Methodology Cell culture and DNA extraction: Small cell lung carcinoma cell lines were obtained from the ATCC. Cell lines were grown in RPMI 1640 medium supplemented with 10% fetal bovine serum and antibiotics. DNA was extracted from cell lines by a proteinase K/SDS digestion followed by phenol/chloroform/isoamyl alcohol extractions either manually (Sambrook et al., 1989) or using the Applied Biosystems, Inc. DNA extractor model 340A. DNA labeling: Chromosomal DNA was labeled with biotin-14-deoxyadenosine triphosphate or digoxigenin-11-deoxyuridine triphosphate (Boehringer Mannheim) using the Gibco/BRL Bio-Nick kit. Reactions were performed for 1 hr. at 15° C. according to the manufacturer's instructions, using a range of DNAse I/Pol I concentrations in order to generate DNA fragments ranging from 200 bp to 2.3 kb (optimal for CGH).

Comparative genomic hybridization: Hybridizations were performed essentially as in Kallioniemi et al., supra. Normal human male lymphocyte metaphase preparations were denatured in 70% formamide and 2× SSC (1× SSC is 0.15M NaCl and 0.015 Na citrate (pH 7)) at temperatures ranging from 72° C. to 78° C. for 2.5 to 10 minutes, depending on the age and quality of the slides. The slides were then dehydrated in a sequence of 70%, 85% and 100% ethanol washes. The slides were air-dried and incubated at 37° C. until the probes were applied (less than 5 minutes). One hundred and twenty nanograms of biotinylated SCLC cell line DNA, 120 ng digoxygenin-labeled normal reference DNA and 5 µg of Cot-1 blocking DNA (Gibco/BRL) were precipitated with ethanol. The pellet was resuspended in 3 µl of $dH_2O$ and mixed with 7 µl of denaturation buffer to give a final concentration of 50% formamide, 10% dextran sulfate and 2× SSC (pH 7). This probe mixture was denatured for 5 minutes at 77° C. and incubated at 37° C. for several minutes before being applied to the metaphase spreads. Cover slips were applied and sealed to the slides with rubber cement, and the slides were incubated in a humidified chamber for 3 days at 37° C.

Slides were washed at 45° C. in three changes of 50% formamide/2× SSC (pH 7), followed by two washes with 2× SSC and one of 0.1× SSC (10 minutes in each wash). All subsequent manipulations were at room temperature. The slides were washed for five minutes in 2× SSC and blocked for 5 minutes in 2× SSC+1% BSA (Sigma Pentax Fraction V). The slides were then immunohistochemically stained with 5 µg/ml FITC-avidin (a green fluorochrome; Vector Laboratories, Burlingame, Calif.) and 2 µg/ml anti-digoxigenin rhodamine (a red fluorochrome; Boehringer Mannheim) in 2× SSC+1% BSA for 30 minutes in the dark. The slides were then washed in the dark for 10 minutes successively in each of the following: 4× SSC, 4× SSC containing 0.1% Triton X-100 (Fluka Chemika), 4× SSC and PN (0.1M $NaH_2PO_4$, 0.1M $Na_2HPO_4$ and 0.1% NP-40). The slides were drained on a paper towel, and 7.5 µl of a solution of 0.1 µM 4,6-di-amino-2-phenylindole (DAPI) was applied. Cover slips were applied and sealed with nail polish.

Image Acquisition and Processing: The slides were examined using a Zeiss Axioplan fluorescence microscope. Metaphases were photographed and stored as three color images (DAPI, FITC and rhodamine) using a cooled charge-coupled device camera (Photometrics, Tucson, Ariz.) interfaced with a Sun 4/330 work station using the Quantitative Image Processing System (QUIPS). Chromosomes were identified based on the DAPI banding patterns (Kallioniemi et al., 1992). The green to red fluorescence ratio profiles were determined by integration of the fluorescence intensity along the axis of each chromosome (Kallioniemi et al, 1992).

Figure 1B:
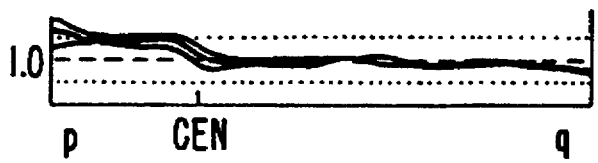
Figure 1C:
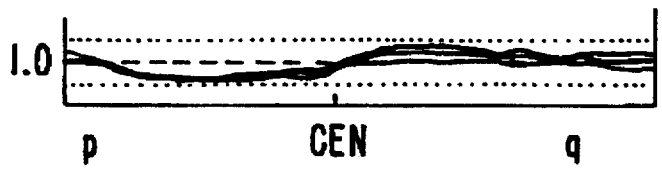
Figure 1D:
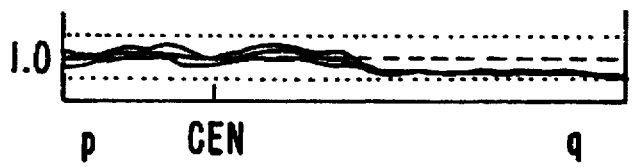
Figure 1E:
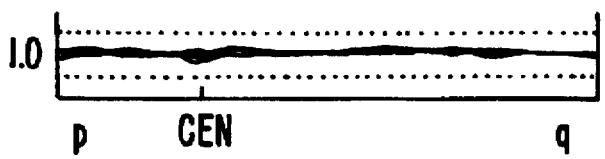

Precise assignment of copy number increases and decreases to chromosomal bands was accomplished by looking for green or red chromosomal regions, respectively, and noting their X and Y coordinates. The DAPI bands corresponding to these regions were then determined by finding the same coordinates in the DAPI image. The extent and location of each copy number change was then plotted on an idiogram showing a schematic representation of the chromosomes G-banding pattern.
Comparison of CGH data FIG. 1 shows representative CGH data illustrating DNA copy number abnormalities detected using CGH. Representative green to red fluorescence ratios corresponding to the red and green digital images of individual chromosomes are shown. Panel A shows a major region of increased copy number relative to normal DNA on chromosome 8 for the SCLC cell line NCI-H510A at 8q21–22. NCI-HS10A was not known to contain any alterations on chromosome 8. Thus, the centromere proximal copy number increase at 8q21–22 represents a previously unrecognized copy number increase. NCI-H510A cells also contain a minor copy number increase at 8q24, near the map position of the c-myc oncogene. However, Southern hybridization shows that this cell line does not contain a c-myo amplification (Brooks et al. (1987) *Advances in Viral Oncology* 7, 155–172). Thus, the present example demonstrates that NCIH-510A cells contain two copy number increases on chromosome 8 which were previously unknown. Panel B shows that NC-H510A cells have an increased DNA copy number at chromosome 5p. Copy number increases on 5p have not been previously reported to be a frequent cytogenetic alteration in SCLC cells or tumors. However, we observed copy number increases on 5p in 11 of 18 cell lines and in 8 of 10 tumors, making the increase at 5p one of the most common cytogenetic alterations in SCLC cells and tumors. Panels C and D show copy number decreases for the cell line NCI-H211. Copy number decrease at 3p (FIG. 1, panel C) is known to be among the most common genetic alterations in SCLC (Brauch et al. (1987) *N. Engl. J. Med.* 317, 1109–1113; Carbine and Minna (1992) *Advances in Internal Medicine* 37, 153–171.), and it has been suggested that one or more tumor suppressor loci may reside there. FIG. 1, panel D shows a decrease at 4q22–35. Although this has not been repeated previously, we observed decreases at this site in over half (10/18) of the SCLC cell lines tested and in 5 of 10 tumors. For comparison, Panel E shows CGH analysis of chromosome 5 from NCI-H433. This chromosome shows no detectable copy number changes.

FIG. 2 summarizes CGH analyses of increases and decreases in DNA copy number in 18 SCLC cell lines, including 8 classic (radiosensitive) and 10 variant (radioresistant) lines. Common copy number changes (i.e. those occurring in >30% of cell lines) are shown in Table 1. The regions listed in Table 1 represent the smallest area on each chromosome arm that is altered in a large number of the cell lines. For example, DNA copy number increases occur on the q arm of chromosome 8 in 12/18 cell lines. However, the extent of the altered region is somewhat different among the cell lines (FIG. 2). The region of most common abnormality is listed as 8q24 because this region, which includes the most distal 3 Giemsa bands (8q24.1, 8q24.2, and 8q24.3 respectively) on 8q, is the minimal region of overlap among cell lines showing a DNA copy number increase in this area. Centromeric regions have not been included in the summaries in FIG. 2 and Table 1 because CGH analyses are not informative in these regions (hybridization is almost completely inhibited in these regions by the excess unlabeled Cot-1 DNA included during hybridization). We have confirmed that most of the alterations identified here in cell lines also occur in small cell lung tumors. The abnormalities found frequently in the cell lines that have been identified in tumors to date are indicated by a "+" in the "Tumor" column in Table 1.

DNA copy number alterations

DNA copy number changes detected in 18 SCLC cell lines are summarized in FIG. 2 and Table 1. Some of these occur at regions previously reported to be aberrant in SCLC. For example, copy increases are seen in 10 of 18 cell lines at 1p22–32, the site of L-myc, and in 7 of 18 cell lines at 2p24–25, the site of N-myc. We also observed copy number increases in 9 of 18 cell lines at 6q22 and in 12 of 18 cell lines at 8q24, the sites of the c-myb and c-myc oncogenes, respectively. These oncogenes have been shown to be amplified in many SCLC tumors and cell lines (Little et al. (1983), *Nature* 306, 194–196; Griffin et al. (1985) *Cancer Research* 45, 272–275). We observed copy number decreases on 3p in 15 of 45, cell cell lines, a genetic alteration that ie frequently observed cytogenetically in SCLC (Whang-Peng et al. (1982), *Cancer Genetics and Cytogenetics* 6, 119–134). No tumor suppressor gene has yet been identified on 3p, but LOH studies suggest that there are at least two and possibly three such tumor suppressor genes on this chromosome arm (Carbone and Minna, 1992). We also observed copy number decreases in 7 of 18 cell lines at 13q, and in 12 of 18 cell lines on 17p, the sites of the RB and p53 tumor suppressor genes, respectively. Both of these tumor suppressor have been previously shown to be frequently altered in SCLC (Harbour et al. (1988) *Science* 241, 353–357; Takahashi et al. (1989), *Science* 246, 491–494).

CGH analysis revealed several new sites of frequent DNA copy number increase or decrease. Among the most common sites of copy number increases are 1q24 (11 of 18 cell lines), 5p (11 of 18 cell lines) and Xq26 (10 of 18 cell lines). Many of the amplifications in the 1q24 region overlap with a novel region of amplification at 1q32 commonly found in breast tumors (Kallioniemi et al., (in press.) "Detection and mapping of amplified DNA sequences in breast cancer by comparative genomic hybridization" *Proc. Natl. Acad. Sci. USA*). The copy number increases that occur on chromosome 5p are unusual in that they are frequently high-level increases (in 6 of 11 cases), despite the fact that they apparently involve the entire chromosome arm. Frequent DNA copy number increases on 5p have also been observed in non-SCLC tumors. Other DNA copy number increases were detected at 1p22–32, 2p24–25, 3q22–25, 13q3, 18p11.1–11.2 and 18q21. Newly identified regions of copy number decrease in SCLC include 22q12.1–13.1, 10q26, 16p11.2 and 19p13.3, which are all affected in at least 13 of the 18 cell lines (FIG. 2 and Table 1). Other DNA copy number decreases were detected at 18p and 10p.

TABLE 1

Minimal Overlapping Regions of Common Copy Number Change in SCLC

| | Chromosomal position | Classic | Frequency Variant | Total | Known Gene | Tumor |
|---|---|---|---|---|---|---|
| Copy Number Increases: | 8q24.1 | 6/8 | 6/10 | 12/18 | c-myc (8q24) | + |
| | 5p | 4/8 | 7/10 | 11/18 | | + |
| | 1q24 | 4/8 | 7/10 | 11/18 | | + |
| | Xq26 | 4/8 | 6/10 | 10/18 | | + |
| | 1p22–32 | 2/8 | 8/10 | 10/18 | L-myc (1p32) | + |
| | Xp22.1 | 3/8 | 6/10 | 9/18 | | |
| | 6q22 | 4/8 | 5/10 | 9/18 | c-myb (6q22) | + |
| | 20p12–13 | 6/8 | 3/10 | 9/18 | | |
| | 11q14–22.2 | 3/8 | 6/10 | 9/18 | | |
| | 7p21 | 3/8 | 5/10 | 8/18 | | |
| | 7q31.2–31.3 | 3/8 | 5/10 | 8/18 | | |
| | 14q12–13 | 2/8 | 6/10 | 8/18 | | |
| | 14q31 | 2/8 | 6/10 | 8/18 | | |
| | 2p24–25 | 1/8 | 6/10 | 7/18 | N-myc (2p24) | |
| | 3q22–25 | 1/8 | 6/10 | 7/18 | | + |
| | 18q21 | 6/8 | 1/10 | 7/18 | | + |
| Copy Number Decreases: | 22q12.1–13.1 | 6/8 | 10/10 | 16/18 | | + |
| | 3p13–14 | 8/8 | 7/10 | 15/18 | * | + |
| | 3p21.3 | 8/8 | 6/10 | 14/18 | * | + |
| | 10q26 | 6/8 | 7/10 | 13/18 | | + |
| | 16p11.2 | 4/8 | 9/10 | 13/18 | | + |
| | 19p13.3 | 6/8 | 7/10 | 13/18 | | + |
| | 17p | 5/8 | 7/10 | 12/18 | p53 (17p13) | + |
| | 16q11.22 | 7/8 | 4/10 | 11/18 | | + |
| | 4q24–26 | 5/8 | 5/10 | 10/18 | | + |
| | 15q11–14 | 6/8 | 4/10 | 10/18 | | + |
| | 19q13.3–13.4 | 3/8 | 7/10 | 10/18 | | + |
| | 10p | 7/8 | 2/10 | 9/18 | | + |
| | 13q11–13 | 3/8 | 4/10 | 7/18 | RB (13q14) | + |

Note:
In Table 1, chromosomal copy number changes occurring in greater than 30% (6/18) cell lines are listed, with the relative distribution in classic and variant cell lines indicated. The chromosomal positions of the copy number changes were assigned based on comparison of the two-color (red and green) comparative genomic hybridization images with the DAPI banding image and based on quantification of green to red ratios along each chromosome axis. The frequency of each copy number change in classic and variant cell lines is based on the data presented in FIG. 2. The oncogenes and tumor suppressor genes listed in the "Known Gene" column are those previously shown to be affected in SCLC cell lines and/or tumors. The "*" symbol in the rows for 3p copy number decreases refers to several as yet unidentified tumor suppressor genes in this region. A "+" symbol in the "Tumor" column indicates that this alteration is observed in at least 30% (3/10) of the SCLC tumors analyzed so far.

changes were assigned based on comparison of the two-color (red and green) comparative genomic hybridization images with the DAPI banding image and based on quantification of green to red ratios along each chromosome axis. The frequency of each copy number change in classic and variant cell lines is based on the data presented in FIG. 2. The oncogenes and tumor suppressor genes listed in the "Known Gene" column are those previously shown to be affected in SCLC cell lines and/or tumors. The "*" symbol in the rows for 3p copy number decreases refers to several as yet unidentified tumor suppressor genes in this region. A "+" symbol in the "Tumor" column indicates that this alteration is observed in at least 30% (3/10) of the SCLC tumors analyzed so far.

Example 2

Correlation of genomic amplifications and deletions with radioresistance

An important reason for analyzing the genetic alterations in SCLC cell lines was to identify specific changes that correlate with phenotypes of these cell lines, including their resistance to ionizing radiation. Over sixty percent of all cancer patients are treated with ionizing radiation during the course of therapy and yet no reliable predictive assays for tumor radioresponsiveness are currently available (Weichselbaum (1991) *Important Advances in Oncology* 73–83) The radioresponsiveness of tumors in vivo varies considerably within one histological type such as SCLC. In vivo radioresponsiveness is a complex phenomenon, involving factors such as the degree to which the tumor is hypoxic (and, therefore, radioresistant), the kinetics of tumor growth, and the level of tumor differentiation. Despite these complications, the failure of radiotherapy to achieve local control of tumor growth is correlated with radioresistance in cell lines derived from both soft tissue sarcomas and head and neck carcinomas (Weichselbaum et al. (1990), *International Journal of Radiation Oncology, Biology, Physics*, 19(2), 313–319). This suggests that tumor radioresistance arising from phenotypic changes caused by genetic aberrations may be an important reason for radiotherapy failure (Weichselbaum, 1991, Suit (1986) *Int. J. Radiat. Oncol. Biol. Phys.*, 12, 453–458). Localization of DNA copy number aberrations that correlate with radioresponse allows for a simple predictive assay for in vivo tumor radioresistance and may lead to the discovery of specific genes which correlate to radioresistance, as well as the development of new procedures for overcoming radioresistance.

Using the methods described above in Example 1, We have identified several DNA copy number changes that correlate well with the "variant" SCLC phenotype (Table 2), which is associated with increased radioresistance (Carmichael et al. (1989) *Eur. J. Cancer Clin. Oncol.* 25, 527–534). Copy number gains on 1p22–32, 2p24–25 and 3q22–25 and losses 18p are preferentially seen in cell lines of the variant phenotype (Chi-square p value <0.1), whereas gains at 13q3, 18p11.1–11.2, and 18q21 and losses at 10p are preferentially seen in cell lines of the classic phenotype (Chi-square p value <0.1). Some of these loci may contain genes that play a role in radioresistance or other aspects of the variant phenotype. Since the variant phenotype includes a number of morphological and biochemical characteristics, it is possible that the genetic alterations leading to this phenotype involve transcription factors or other regulatory proteins whose overexpression switches the tumor cell to an alterative developmental fate. For instance, overexpression of the c-myc oncogene in classic SCLC lines by DNA transfection has been shown to result in a partial variant phenotype (Johnson et al. (1986), *Journal of Clinical Investigation* 78, 525–532). Our results indicate that a good correlation exists between the variant phenotype and increased copy number at 1p22–32 (L-myc) and 2p24–25 (N-myc). The radioresistant phenotype of variant SCLC cell lines might be explained by an increase in expression of DNA repair enzymes capable of repairing the double strand breaks caused by ionizing radiation or, perhaps, by a change in the cell cycle distribution, a parameter that is known to affect radioresistance (Hall (1988) *Radiobiology for the Radiologist*, 3rd edition, J. B. Lippincott, Philadelphia, Pa.). In addition to L-myc, the GADD45 gene, which was identified based on the fact that it is transcriptionally activated in response to ionizing radiation (Fornace et al. (1989), *Mol. Cell. Biol.* 9, 4196–4203) maps to the site of variant-specific amplification observed in these studies. Finally, the regional amplification observed at 11q23 which occurred in 4 variant cell lines and no classic cell lines overlaps the Ataxia Telangiectasia locus (Gatti et al. (1988), *Nature* 336, 577–580). Standard FISH probe technology will allow investigators to determine whether these genes are involved in the radioresistance phenotype of variant cell lines.

TABLE 2

Copy number changes that correlate with the variant or classic phenotype

| | Chromosoma | Classic lines | Frequency Variant lines | Total | Chi-Square P-value |
|---|---|---|---|---|---|
| Variant-specific Copy Number Increases | 1 position | | | | |
| | 1p22–32 | 1/8 | 8/10 | 9/18 | <0.05 |
| | 2p24–25 | 1/8 | 6/10 | 7/18 | <0.1 |
| | 3q22–25 | 1/8 | 6/10 | 7/18 | <0.1 |
| Copy Number Decreases | 18p | 0/8 | 5/10 | 5/10 | <0.025 |
| Classic-specific Copy Number Increases | 13q3 | 4/8 | 1/10 | 5/18 | <0.1 |
| | 18p 11.1–11.2 | 4/8 | 1/10 | 5/18 | <0.1 |
| | 18q21 | 5/8 | 1/10 | 6/18 | <0.1 |
| Copy Number Decreases | 10p | 6/8 | 2/10 | 8/18 | <0.1 |

Example 3

Genetic aberrations in non-small cell lung cancers (N-SCLC) detected by CGH

In order to detect genetic aberrations in N-SCLCs, tumor DNAs were analyzed using CGH as per Example 1. DNAs from five N-SCLC cell lines (PC3, PC7, PC13: adenocarcinomas, PC10:Squamous cell carcinoma, and PC14: large cell carcinoma) and 20 primary lung cancers (11 adenocarcinomas, 6 squamous cell carcinomas, 1 small cell carcinoma, 1 small+squamous cell combined type carcinoma, and 1 large cell carcinoma) were used in the CGH analysis to generate green/red intensity profiles of each chromosome analyzed. Chromosomal regions showing a green/red ratio greater than 1.45 were considered to be amplified, while a green/red ratio of less than 0.75 was considered to contain a deletion.

FIG. 3 shows amplified and deleted chromosomal regions in 5 lung cancer cell lines. FIG. 4 shows the amplified and deleted chromosomal regions in 20 primary lung cancers. In cell lines, the frequently amplified regions were 3q (4/5), 5p (3/5), 6p (3/5), 7q (3/5), 8q (3/5), 9q (3/5), and 20p (4/5) The frequently deleted regions were 3p (2/5), 4q (3/5), 6q (2/5), 9p (2/5), 9q (2/5), 10p (3/5), 11q (2/5), 13q (3/5), 14q (3/5), 15q (2/5), 17p (3/5), 18q (3/5), 22q (2/5) and X (3/5). In the primary lung cancers which were examined, the frequently amplified regions were 3q (6/20), 5p (6/20), 7p (3/20) and 8q (5/20). In addition, one case of 20q amplification that had been previously reported for breast cancer was observed in an adenocarcinoma. The frequently deleted regions in the primary tumors were 1p (11/20), 10q (4/20), 16p (8/20), 17p (9/20), 19p (14/20), 19q (15/20) and 22q (6/20). The regions which were found to be amplified in both primary tumors and N-SCLC cell lines are 3q, 5p, 7p, 7q, 8q and 9q.

Some known oncogenes, for instance, MYC (C-myc) (8q24), EGFR (V-erb-b) (7p12), KRAS1P (6p12-p11) and NRASL3 (6pter-p21) are located in the commonly amplified regions observed in this Example. Additional unknown oncogenes may be located in the chromosomal regions 3q, 5p and 7q. The loci of known tumor suppressor genes APC (5q21–22), WT1 (11p13), RB1 (13q14.2) TP53 (17p13.1 and DCC (18q21.1) are involved in the deleted region in cell lines, but most of them are not involved in the primary tumors which were studied herein.

The gain and loss of chromosomal regions and the corresponding correlation with the survival rate of patients with primary non-small cell lung carcinomas are shown in Tables 3 and 4.

TABLE 3

Chromosomal alterations in N-SCLC cell lines and primary tumors with corresponding mortality.

| Name | Histology | P-stage | Chromosomal gain | Chromosomal Loss | Frequent Loss | Recurrance | Survival |
|---|---|---|---|---|---|---|---|
| PC3 | AD | | 1q, 2q, 6q, 15 | 8q, 9q, 11p, 13q, 14g, 18q | 17p, 19q | | |
| Pc7 | AD | | 1p, 1q, 3q, 4p, 4q, 6p, 7p, 7q, 8p, 8q, 9q, 12q, 13q, 15, 20p | 3p, 4q, 6q, 11q, 18g | 17p, 22q | | |
| PC10 | SQ | | 1q, 2p, 2q, 3q, 5p, 7p, 7q 20p | 1p, 1q, 4p, 4q, 5q, 8p, 9q, 10p, 13, Xp | 19p | | |
| PC13 | AD | | 3q, 5p, 6p, 7q, 8q, 9q, 20p | 2p, 3p, 4q, 6q, 10p, 11q, 14q, 18q, 21q, Xp, Xq | 16p, 17p, 22q | | |
| PC14 | LA | | 1p, 2p, 2q, 3p, 3q, 5p, 6p, 9q, 10q, 14, 16q, 20p | 9p, 10p, 21q | (31) | | |
| NCI-H69 | SM | | 1q, 3q, 6p, 6q, 7q, 9p, 11p 13q, 18p, 18q | 1p, 2p, 2q, 3p 3q, 4p, 4q, 7p, 8q, 10p, 10q, 13q, 20q | 17p | | |
| M.H. | Fibro-sarcoma | IV | 5q, 13q, 18p, 18q | 16q | 16p, 17p, 19p, 19q | | |
| O.F. | Renal Cell Carcinoma | IV | 9p | (–) | 22p, 22q | | |
| M.T. | Neuri-noma | Benign | (–) | (–) | 22q | | |
| Y.T. | AD | IIIA | Xp, Xq | 9q, 10q | 1p, 19p, 19q | (+) 31 M | Alive (43) |
| M.T. | AD | II | 5p | 1p | 22q | (–) renal failure (af) | Dead (1M) |
| M.T. | AD | IV (pm) | 15q | 2q, 10q, 14q | 17p | (–) pneumonia | Dead (2M) |
| Y.A. | AD | IIIA | 3q | (–) | 1p, 16p, 19p, 19q | (–) | Alive (50M) |
| K.H. | AD | IIIB | 5p, 7p, 14q, 20q | 2q | 16p, 17p, 19p, 19q, 22q | (+) | Dead (4M) |
| K.K. | AD | IIIA | 3q, 5q, 8q, 15q | 8p, 9q, 10p, 10q, 14q | 17p, 19p, 22q | (+) | Dead (14M) |
| Y.K. | AD | IIIA | (–) | (–) | 1p, 19p, 19q, 22q | (+) | Dead (31M) |
| K.K. | AD | I | 2q | (–) | 1p, 16p, 19p, 19q | (–) | Alive (45M) |
| G.T. | AD | II | 5p, 5q, 7p, 8q | 8p | 19p, 19q | (–) | Alive (50M) |
| Y.S. | AD | IIIA | (–) | (–) | 19p, 19q | (+) | Dead (6M) |
| T.M. | AD | IIIA | 1q, 6p, 15q, 21q | (–) | 19p, 19q | (?) | Alive (30M) |
| K.Y. | SQ | IIIA | 3q | (–) | 1p | (+) | Dead (40M) |
| K.H. | SQ | IIIB | 3q, 9p | 9q, 12q | 1p, 17p, 19p, 19q | (+) 36M | Dead (40M) |
| H.K. | SQ | IIIA | 1q, 5p, 7p, 8q | (–) | 1p, 17p, 19p, 19q, 22q | (?) | Alive (3M) |
| H.I. | SQ | IV | (–) | (–) | 1p, 17p, 19q, 22q | (+) | Dead (24M) |

TABLE 3-continued

Chromosomal alterations in N-SCLC cell lines and primary tumors with corresponding mortality.

| Name | Histology | P-stage | Chromosomal gain | Chromosomal Loss | Frequent Loss | Recurrance | Survival |
|---|---|---|---|---|---|---|---|
| S.K. | SQ | IIIA | 3q, 5p, 6p, 6q, 7q, 8q, 12p, 12q, Xp, Xq | (−) | 1p, 16p, 16q, 17p | (+) | Dead (4M) |
| S.I. | SQ | IIIA | (−) | (−) | 1p, 16p, 19p, 19q | (−) MRSA | Dead (3M) |
| H.T. | SM | I | 5p, 8q | 4q, 5q, 10p, 10q, 16g | 16p, 17p | (−) | Alive (23M) |
| M.H. | SM + SQ | IIIA | 3q | 3p, 5q, 16q | 16p, 17p, 19p, 19q, 22q | (−) sepsis | Dead (1M) |
| S.T. | LA | I | (−) | (−) | 1p, 16p, 19p, 19q, | (−) | Alive (33M) |

Ad = Adenocarcinoma, SQ = squamous cell carcinoma, SM = small cell carcinoma, LA = large cell carcinoma
Deletion = excludes region around centromeres.

TABLE 4

Correlation of survival rate to gain or loss of chromosomal region.

| Chromosomal gain/no gain | Chromosomal Loss/no loss | Number | Wilcoxon N.S. | Cox-Mantel N.S. | 1 year survival rate/3 year survival rate | Median Survival Term (months) |
|---|---|---|---|---|---|---|
| 3q gain | | 6 | .04132 | .782009 | 80%/60% | 14 |
| 3q no gain | | 14 | | | 80%/54.9% | 23 |
| 5p gain | | 6 | .4545 | .5726 | 50%/50% | 4 |
| 5p no gain | | 14 | | | 90.9%/62.3% | 30 |
| 8q gain | | 5 | .1749 | .3987 | 75%/50% | 4 |
| 8q no gain | | 15 | | | 81.8%/62.3% | 30 |
| | 1p loss | 11 | 1.2559 | .6971 | 88.9%/66.7% | 33 |
| | 1p no loss | 9 | | | 66.7%/50% | 4 |
| | 16p loss | 8 | .6570 | .6037 | 66.7%/66.7% | 4 |
| | 16p no loss | 12 | | | 88.9%/53.3% | 24 |
| | 17p loss | 9 | 1.522 | 2.4759 | 66.7%/25.0% | 4 |
| | 17p no loss | 11 | | | 88.9%/76.2% | 33 |
| | 22q loss | 7 | $p < .05$ (2.1833) | $p < .01$ (2.664) | 75%/0% | 4 |
| | 22q no loss | 13 | | | 81.8%/81.8% | 30 |

Note:
the relationship between pathological stage and survival rate is as follows: p-stage I + II (n = 5) 1 year survival rate = 100%, 3 year survival rate = 100% median survival term = 23 months; p-stage III + IV (n = 15) 1 year survival rate = 75%, 3 year survival rate = 48.6%, median survival rate = 14 months (Wilcoxon N.S. = 0.3061; Cox-Mantel ($p < .05$) = 1.990).
The relationship between the number of chromosomal gains and the survival rate in this study is as follows: gains ≦ 3 (n = 14) 1 year survival rate = 90%, 3 year survival rate = 67.5%, median survival term = 24 months. For gains ≧ 4 (n = 6) the 1 year survival rate = 60%, 3 year survival rate = 40%, median survival term = 4 months.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of screening for the presence of small cell lung carcinoma cells in a sample, the method comprising:

contacting a nucleic acid sample from a human patient with a probe which binds selectively to a target polynucleotide sequence on a chromosomal region which is deleted in small cell lung carcinoma cells and is selected from the group consisting of 1q24, 5p, and Xq26, or a probe which binds selectively to a target polynucleotide sequence on a chromosomal region which is amplified in small cell lung carcinoma cells and is selected from the group consisting of 22q12.1–13.1, 10q26, 16p11.2, and 19p13.3;

wherein the probe is contacted with the sample under conditions in which the probe binds selectively with the target polynucleotide sequence to form a hybridization complex; and detecting the formation of a hybridization complex.

2. The method of claim 1, wherein the chromosome abnormality is a deletion.

3. The method of claim 1, wherein the chromosome abnormality is an amplification.

4. The method of claim 1, wherein the nucleic acid sample is from a sputum sample from the patient.

5. The method of claim 1, wherein the probe is labeled with digoxigenin or biotin.

6. The method of claim 1, wherein the step of detecting the hybridization complex is carried out by detecting a fluorescent label.

7. The method of claim 6, wherein the fluorescent label is FITC.

8. The method of claim 1, wherein the sample comprises a metaphase cell.

9. A method of screening for the presence of non-small cell lung carcinoma cells in a sample, the methods comprising:

contacting a nucleic acid sample from a human patient with a probe which binds selectively to a target polynucleotide sequence on a chromosomal region which is deleted in non-small cell lung carcinoma cells and is selected from the group consisting of 1p, 16p, 17p, and 22q or a probe which binds selectively to a target polynucleotide sequence on a chromosomal region which is amplified in non-small cell lung carcinoma cells and is selected from the group consisting or 3q, 5p, and 8q;

wherein the probe is contacted with the sample under conditions in which the probe binds selectively with the target polynucleotide sequence to form a hybridization complex; and detecting the formation of a hybridization complex.

10. The method of claim 9, wherein the nucleic acid sample is from a sputum sample from the patient.

11. The method of claim 9, wherein the probe is labeled with digoxigenin or biotin.

12. The method of claim 9, wherein the step of detecting the hybridization complex is carried out by detecting a fluorescent label.

13. The method of claim 12, wherein the fluorescent label is FITC.

14. The method of claim 9, wherein the sample comprises a metaphase cell.

* * * * *